(12) United States Patent
Chen (10) Patent No.: US 6,616,640 B2
(45) Date of Patent: Sep. 9, 2003

(54) SYRINGE WITH PLUNGER ANTI-DETACHMENT MECHANISM

(76) Inventor: Marina Ling-Ko Chen, 550 Sourth Hill St., Ste. 913, Los Angeles, CA (US) 90013

( * ) Notice: Subject to any disclaimer, the term of this patent is extended or adjusted under 35 U.S.C. 154(b) by 0 days.

(21) Appl. No.: 10/038,457

(22) Filed: Jan. 7, 2002

(65) Prior Publication Data

US 2003/0130623 A1 Jul. 10, 2003

(51) Int. Cl.[7] ............................................. A61M 5/315
(52) U.S. Cl. ........................ 604/220; 604/181; 604/187
(58) Field of Search ............................. 604/19, 27, 36, 604/38, 73, 131, 141, 152, 154, 155, 156, 164.01, 181–243, 264, 272; 606/167, 181, 184, 185, 186; 600/573, 576

(56) References Cited

U.S. PATENT DOCUMENTS

| | | | | |
|---|---|---|---|---|
| 5,300,038 A | * | 4/1994 | Haber et al. | 604/187 |
| 5,531,694 A | * | 7/1996 | Clemens et al. | 604/110 |
| 5,632,733 A | * | 5/1997 | Shaw | 604/195 |
| 5,800,403 A | * | 9/1998 | Pressly et al. | 604/195 |
| 5,843,034 A | * | 12/1998 | Redfern et al. | 604/110 |
| 5,957,897 A | * | 9/1999 | Jeffrey | 604/223 |
| 6,206,857 B1 | * | 3/2001 | Chen | 604/195 |

* cited by examiner

Primary Examiner—Brian L. Casler
Assistant Examiner—Jennifer Maynard
(74) Attorney, Agent, or Firm—Raymond Y. Chan; David and Raymond Patent Group (57) ABSTRACT

A plunger anti-detachment mechanism incorporates with a syringe which includes a hollow barrel, a hollow needle held at one end of the hollow barrel, and a plunger adapted to coaxially travel through the barrel. The plunger anti-detachment mechanism includes at least a locking stopper radially extended on the barrel and at least a resilient arm, having a locking latch outwardly extended therefrom, radially extended from the plunger wherein the resilient arm is adapted to move from an unlocked position to a locked position. At the unlocked position, the locking latch is moved away from the locking stopper such that the plunger is capable of freely traveling through the barrel, and that at the locked position, the locking latch is extended to the locking stopper so as to block up an axial movement of the plunger with respect to the barrel and interlock the plunger with the barrel.

20 Claims, 7 Drawing Sheets

SYRINGE WITH PLUNGER ANTI-DETACHMENT MECHANISM

BACKGROUND OF THE PRESENT INVENTION

1. Field of Invention

The present invention relates to syringes, and more particularly to a syringe with plunger anti-detachment mechanism which securely locks up the plunger in the hollow barrel after use for preventing the plunger detaching from the hollow barrel accidentally, so as to prevent the used needle from contacting with anybody.

2. Description of Related Arts

It is well known that the needles of syringes are frequently intended for disposal after single use and rendered inoperative to prevent accidental injury or re-use with the substantial risk cross-contamination.

There are many conventional syringes employed with a needle retraction device which enables the used needle being retracted inside the barrel. For example, U.S. Pat. Nos. 4,650,468 and 4,804,370 each suggests a kind of medical syringe that enables its used needle being retracted inside the barrel by re-pulling out the plunger. U.S. Pat. No. 4,695,274 discloses an improved kind of medical syringe which further includes a spring inside so as to retract the needle inside the barrel.

U.S. Pat. No. 6,206,857 which is invented by the applicant of the present invention provides a syringe with needle retraction arrangement for automatically retracting the hollow needle into a hollow plunger after use that prevents the used needle from contacting with anybody. Moreover, the '857 patent is easy to assembly and has a relatively low manufacturing cost while no air ventilation holes or air space is required in the structure.

However, when the used needle is retracted inside the barrel, the used needle may be exposed if the plunger is accidentally detached from the barrel. Moreover, there is no guarantee that the used syringe will not be re-used by simply replacing the used needle from the barrel with another set of plunger and needle.

Therefore, some conventional syringe may comprises a locking device in order to lock up the plunger with the barrel, so as to prevent the plunger from being detached from the barrel accidentally. However, the locking device has a major drawback.

In order to fill the liquid form medicine in the barrel, a pulling force must be applied on the plunger to pull the plunger away from the hollow needle, so as to suck the medicine into the barrel through the needle. When the plunger is pushed towards to the needle gradually, the medicine is pushed to eject through the needle which penetrated into a patient's tissue. Therefore, the sucking operation and the ejecting operation require opposed pulling and pushing forces on the plunger with respect to the barrel. However, the locking device may lead to different operational results since the locking device may lock up the plunger during the sucking operation or even during the ejecting operation. Any unwanted operation of the locking device will cause a serious injury to the patient. However, it is unreasonable that the syringe utilizes a complicated locking device to achieve a safety and precise operation thereof, which may largely increase the number of parts and the manufacturing cost and labor, since the syringe is specifically designed for disposable one-time use.

In view of above, conventional syringes have drawback in practical use, and hence there has been a demand for a syringe with a locking device which is improved in both safety and operability.

SUMMARY OF THE PRESENT INVENTION

The main object of the present invention is to provide a syringe with plunger anti-detachment mechanism which locks up the plunger in the hollow barrel after use For preventing the plunger detaching from the hollow barrel accidentally.

Another object of the present invention is to provide a syringe with plunger anti-detachment mechanism which can guarantee the syringe will not be re-used since the used needle is permanently locked in the barrel. Therefore, the syringe is well suited for disposable one-time use.

Another object of the present invention is to provide a syringe with plunger anti-detachment mechanism which does not affect the sucking operation and the ejecting operation of the syringe so as to prevent the plunger being stuck in a mid-way of the operation with respect to the barrel accidentally.

Another object of the present invention is to provide a syringe with plunger anti-detachment mechanism wherein the hollow needle is automatically retracted into the hollow plunger after use so as to prevent the used needle from contacting with anybody.

Another object of the present invention is to provide a syringe with plunger anti-detachment mechanism which is easy to assembly and has a relatively low manufacturing cost.

Accordingly, in order to accomplish the above objects, the present invention provides a syringe, which comprises:

a hollow barrel having an open end portion, a needle mounting portion, a tubular needle hub extending from the needle mounting portion to provide a needle passageway therethrough;

a hollow needle having a tissue penetrating end and a tip end thereof affixed with a cylindrical tip head, wherein the tip head of the hollow needle is disposed in the needle mounting portion with the tissue penetrating end penetrating through the needle passageway;

a mounting seat integrally affixed within the needle mounting portion of the hollow barrel for securely mounting the tip head of the hollow needle in position;

a hollow plunger adapted to travel through the hollow barrel, the hollow plunger having an outer closed end and an inner end inserted in the hollow barrel through the open end portion of the hollow barrel;

a needle retraction arrangement disposed in the hollow barrel for retracting the hollow needle into the hollow plunger; and a plunger anti-detachment mechanism, comprising:

at least a locking stopper radially provided at an inner annular wall of the hollow barrel; and at least a resilient arm, having a locking latch outwardly extended therefrom, radially extended from the hollow plunger wherein the locking latch of the resilient arm is adapted to normally slide along an inner annular wall of the hollow barrel until the locking latch is extended to the locking stopper so as to block up an axial movement of the hollow plunger with respect to the hollow barrel, so that the hollow plunger is interlocked with the hollow barrel to retain the hollow needle in the hollow plunger.

DETAILED DESCRIPTION OF THE PREFERRED EMBODIMENT

Referring to FIGS. 1 to 4 of the drawings, a syringe 10 with plunger anti-detachment mechanism 80 according to a first preferred embodiment of the present invention is illustrated, which comprises a hollow barrel 20, a hollow needle 30, a mounting seat 60, a needle retraction arrangement 1, and a hollow plunger 70.

Figure 1:
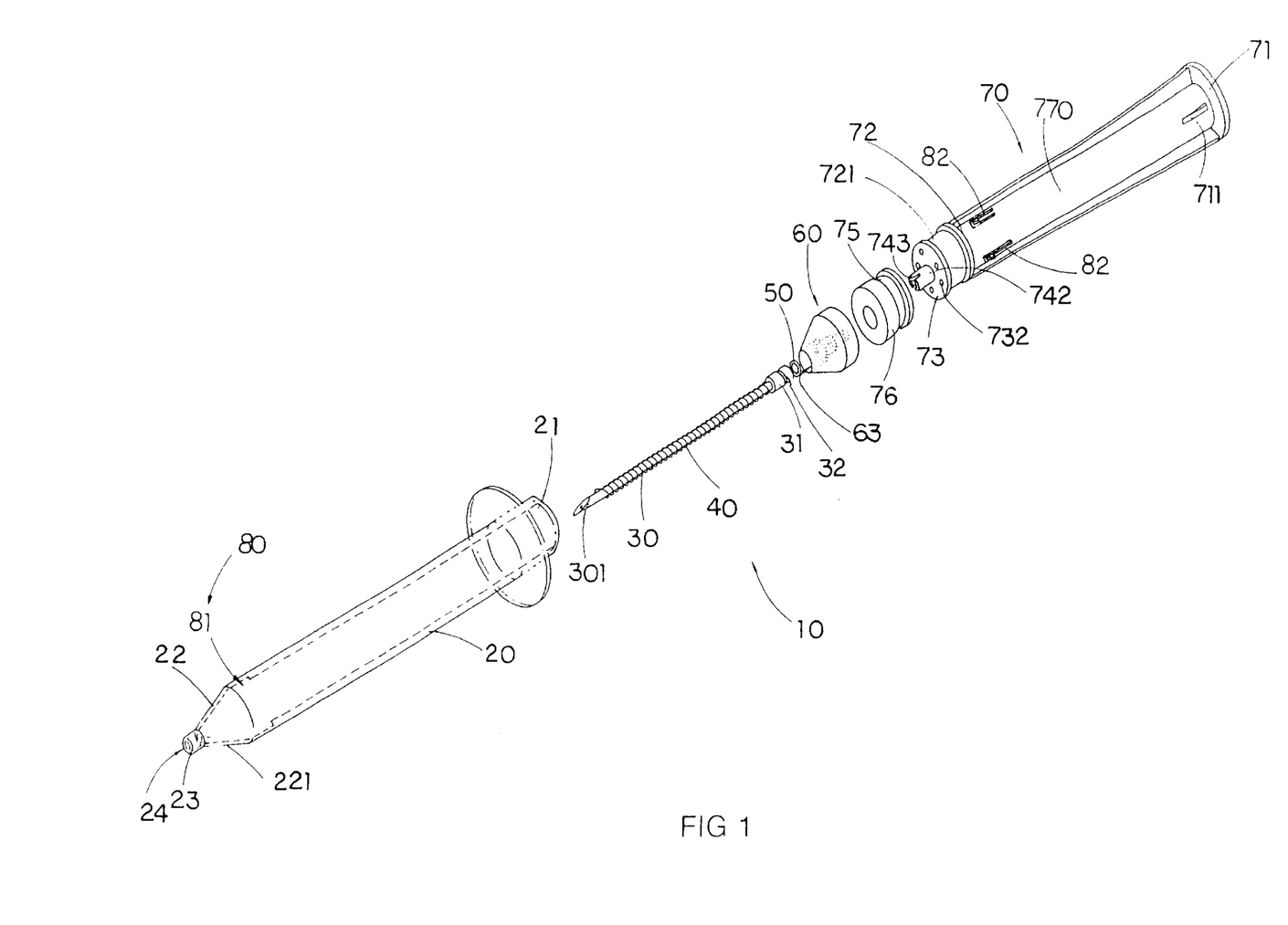
FIG. 1 is an exploded perspective view of a syringe with plunger anti-detachment mechanism according to a first preferred embodiment of the present invention.
Figure 2:
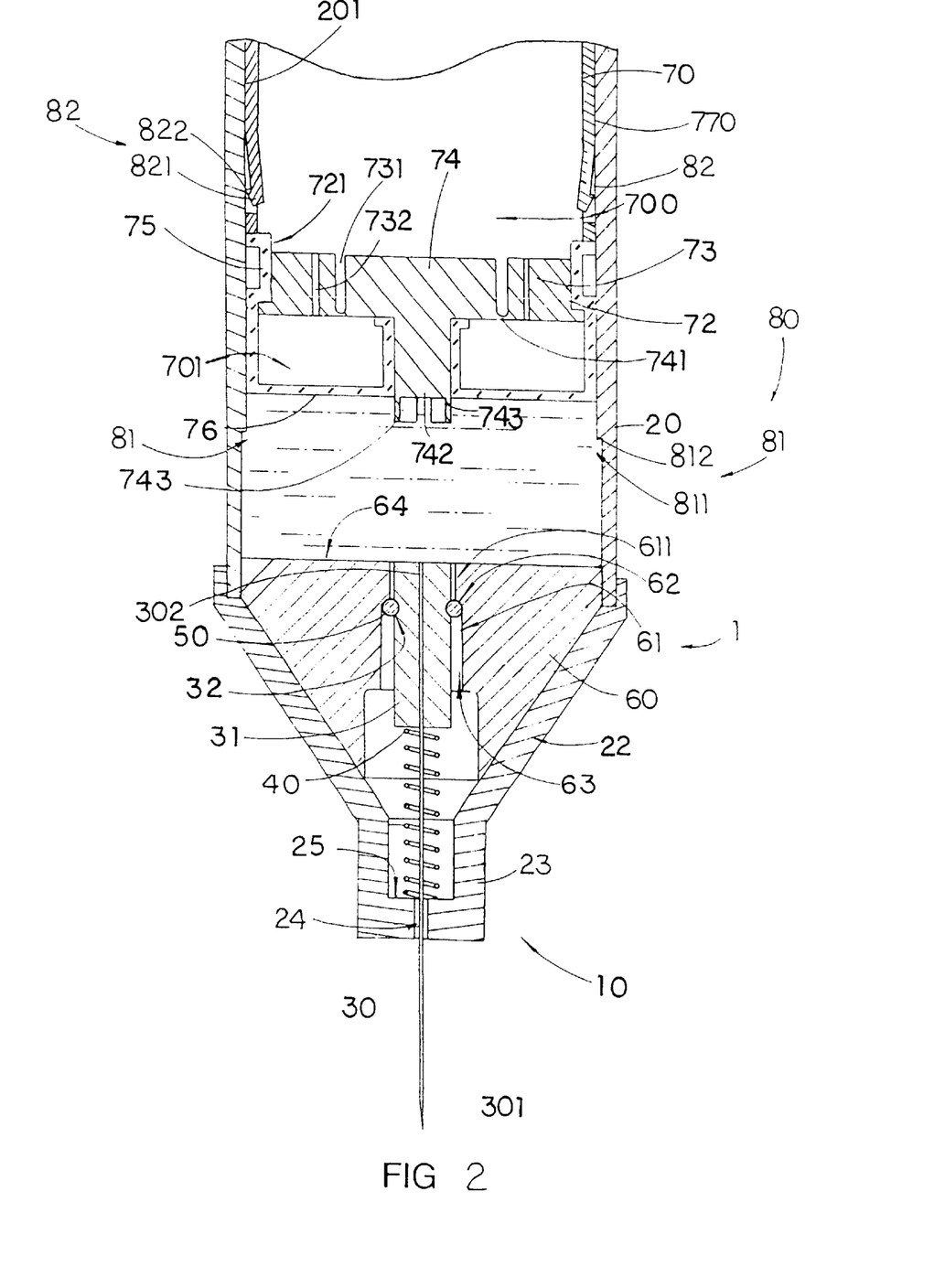
FIG. 2 is a partial sectional view of the syringe, while it is filled with medicine, according to the above first preferred embodiment of the present invention, illustrating the hollow plunger in an unlocked position.

The hollow barrel 20 has an open end portion 21, a needle mounting portion 22, and a tubular needle hub 23 extending from the needle mounting portion 22 to provide a needle passageway 24 therethrough and an end shoulder 25 radially extended inwardly from a free end 221 of the needle mounting portion 22, as shown in FIGS. 1 and 2.

The hollow needle 30 has a tissue penetrating end 301 and a tip end 302 thereof affixed with a cylindrical tip head 31 which has a shallow ring groove 32 provided thereon, wherein the tip head 31 of the hollow needle 30 is disposed in the needle mounting portion 22 with the tissue penetrating end 31 penetrating through the needle passageway 24.

The mounting seat 60 is integrally affixed within the needle mounting portion 22 of the hollow barrel 20 for securely mounting the tip head 31 of the hollow needle 30 in position.

The hollow plunger 70, which is adapted to coaxially travel through the hollow barrel 20, has an outer closed end 71 and an inner end 72 inserted in the hollow barrel 20 through the open end portion 21. The outer close end 71 of the hollow plunger 70 has a plurality of air holes 711 provided thereon, as shown in FIG. 1. The hollow plunger 70 further comprises a closure seat 73 being connected to the inner end 72 of the hollow plunger 70 so as to define a receiving cavity 700 inside the hollow plunger 70.

The needle retraction arrangement 1 is arranged for retracting the hollow needle 30 into the hollow plunger 70, wherein the needle retraction arrangement 1 comprises a compression spring 40 surrounding the hollow needle 30 and having two ends pressing against the end shoulder 25 of the needle hub 24 and the tip head 31 of the hollow needle 30 respectively, and an O-ring 50 removeably resting around the ring groove 32 of the tip head 31 of the hollow needle 30.

Figure 4:
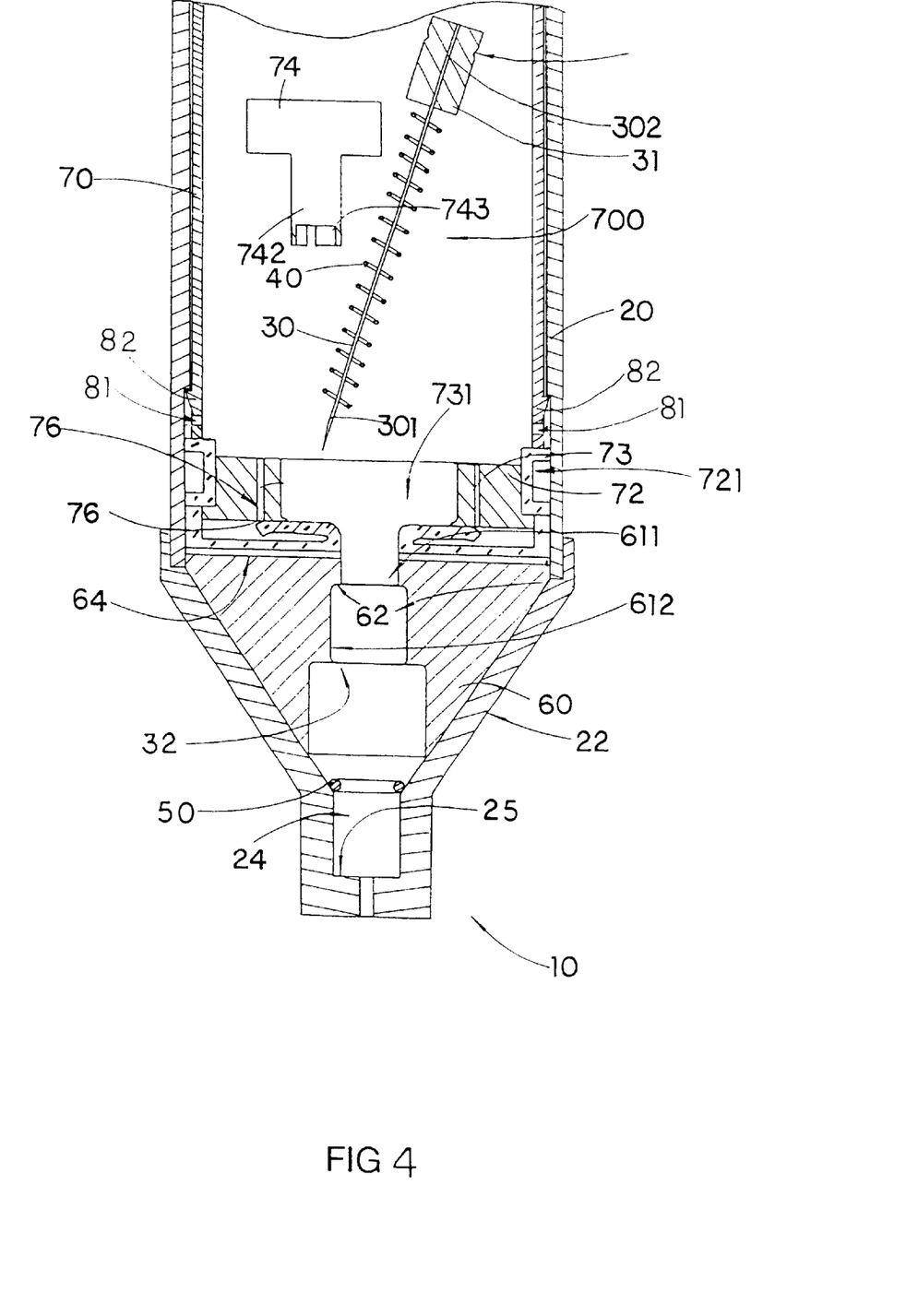
FIG. 4 is a partial sectional view of the syringe, while its needle is retracted inside the plunger, according to the above first preferred embodiment of the present invention, illustrating the hollow plunger interlocked with the hollow barrel.

The plunger anti-detachment mechanism 80 at least a locking stopper 81 radially extended on the hollow barrel 20 and at least a resilient arm 82, having a locking latch 821 outwardly extended therefrom, radially extended from the hollow plunger 70 wherein the resilient arm 82 is adapted to move from an unlocked position to a locked position. At the unlocked position, the locking latch 821 of the resilient arm 82 is moved away from the locking stopper 81 such that the hollow plunger 70 is capable of freely traveling through the hollow barrel 20 in a coaxially movable manner, and that at the locked position, the hollow needle 30 is retracted in the hollow plunger 70 and the locking latch 821 of the resilient arm 82 is extended to the locking stopper 81 so as to block up an axial movement of the hollow plunger 70 with respect to the hollow barrel 20, so that the hollow plunger 70 is interlocked with the hollow barrel 20 to retain the hollow needle 30 in the hollow plunger 70.

According to the preferred embodiment, the locking stopper 81 is embodied to contain a locking groove 811 radially indented on an inner annular wall 201 of the hollow barrel 20 to define a blocking shoulder 812 which is positioned closed to the needle mounting portion 22 thereof.

In order to form the locking stopper 81 on the inner annular wall 201 of the hollow barrel 20, the hollow barrel 20 is constructed to have a tubular body and a hollow cone body integrally attached together in an air tight manner wherein the locking groove 811 is provided on the tubular body by reducing a thickness thereof to define the blocking shoulder 812, as shown in FIG. 2.

The resilient arm 82 is integrally extended on an outer annular wall 770 of the hollow plunger 70 wherein a free end of the resilient arm 82 forms the locking latch 821 having a triangular shaped to define a blocking surface 822 thereof. The locking latch 821 of the resilient arm 82 is adapted to normally slide along the inner annular wall 201 of the hollow barrel 20 in such a manner that when the hollow plunger 70 is pushed down until the locking latch 821 fits in the locking stopper 81, the blocking surface 822 of the resilient arm 82 is biased against the blocking shoulder 812 to lock up the hollow plunger 70 with the hollow barrel 20, so as to prevent the hollow plunger 70 from moving upward.

As shown in FIG. 1, the resilient arm 82 is formed by U-shaped cut cutting through the outer annular wall 770 of the hollow plunger 70 such that a top edge of the resilient arm 82 is integrally extended from the outer annular wall 770 of the hollow plunger 70 while the rest of the edges of the resilient arm 82 are in suspended manner. Therefore, the resilient arm 82 provides an elastic ability that adapted to move towards the receiving cavity 700 of the hollow plunger 70.

Accordingly, the mounting seat 60, as shown in FIG. 2, has an O-ring passage 61 coaxially aligned with the needle hub 23, a top end portion 611 of the O-ring passage 61 reducing diameter to define a stopper shoulder 62 against which the O-ring abuts, wherein a circular gap 63 is formed between the ring groove 32 of the tip head 31 of the hollow needle 30 and an annular wall 612 of the O-ring passage 61, the circular gap 63 having a width smaller than a diameter of the O-ring 50 so as to compress the O-ring 50 between the stopper shoulder 62 and the ring groove 32 and to securely mount the tip head 32 in the O-ring passage 61.

Figure 3:
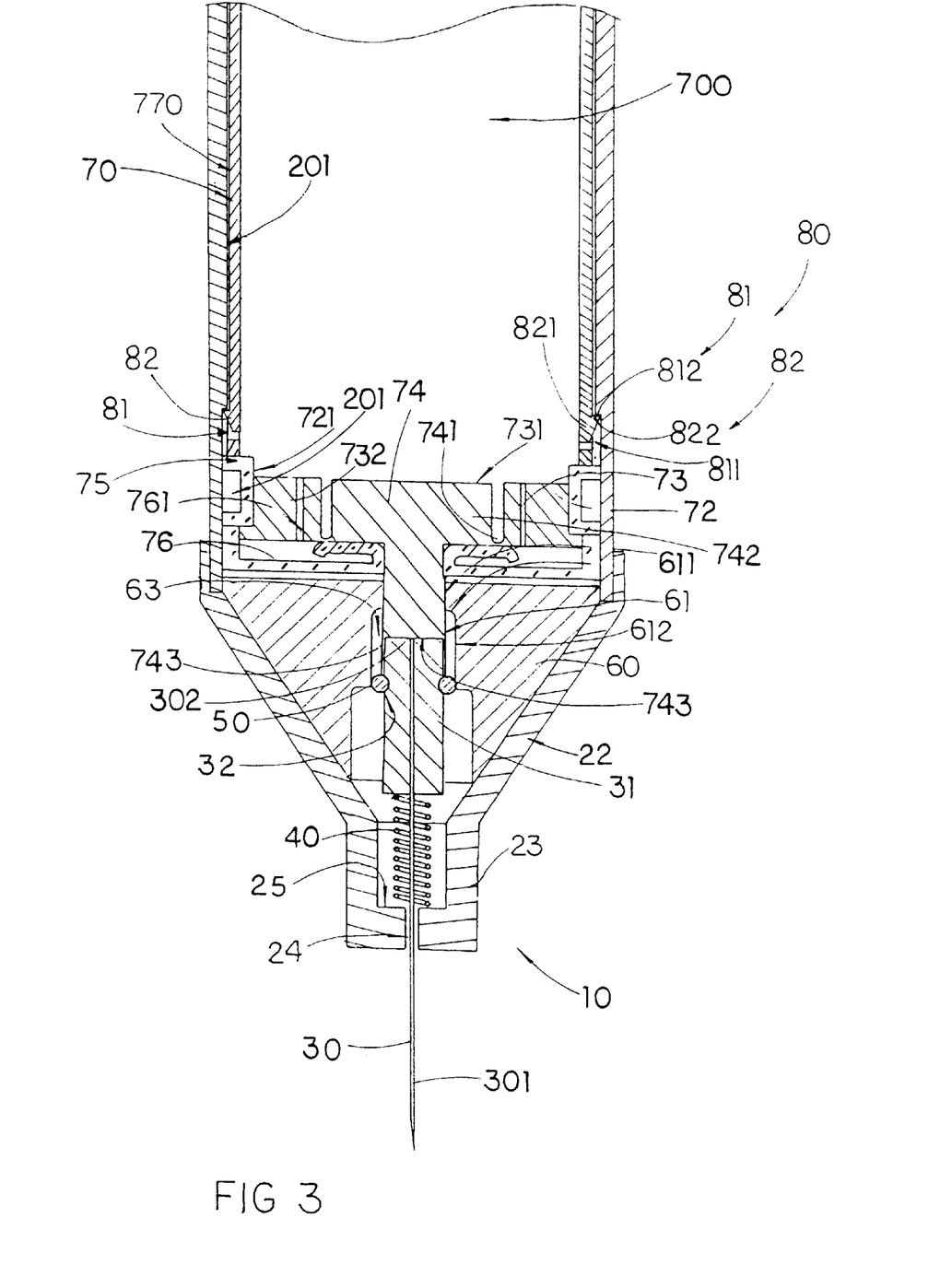
FIG. 3 is a partial sectional view of the syringe, while the medicine is ejected, according to the above first preferred embodiment of the present invention, illustrating the hollow plunger in an unlocked position.

As shown in FIGS. 2, 3, and 4, the closure seat 73 has an entrance aperture 731 positioned above the O-ring passage 61 of the mounting seat 60 and a plurality of air apertures 732 provided around the entrance aperture 731. The entrance aperture 731 is covered by a pusher member 74 which is circumferentially connected with the entrance aperture 731 through a circular thin connecting rib 741 in such a manner that, the thin pusher member 74 is detached to open the entrance aperture 731 when a predetermined pound of urging force is applied to the pusher member 74 and breaks the connecting rib 741.

Therefore, when the closure seat 73 of the hollow plunger 70 is intentionally pushed towards the mounting seat 60, the pusher member 74 presses the tip head 31 as well as the O-ring 50 thereon to slide towards the needle hub 23 and further compress the compression spring 40 to store a resilient force.

According to the preferred embodiment, the pusher member 74 further comprises a pushing stud 742 protruded towards the mounting seat 60 and a plurality of pressing wings 743 spacedly extended from the pushing stud 742 downwardly. The pushing stud 742 has a size adapted to enter the O-ring passage 61 and directly apply pressing force onto the tip head 31 of the needle 30 when the hollow plunger 70 is inwardly pushed towards the mounting seat 60.

As shown in FIGS. 2 to 4, a sealing groove 721 is provided around the inner end 72 for holding a ring shaped sealing member 75 thereon. The sealing member 75, which is made of elastic material such as rubber, fits in the clearance between the inner annular wall 201 of the hollow barrel 20 and the sealing groove 721 so as to ensure air tight and sealing effects of the hollow plunger 70.

The closure seat 73 further comprises a spacer 76 disposed below a bottom surface of the closure seat 73 and extended surrounding the pushing stud 742 of the pusher member 74, wherein an air layer 761 is defined between the bottom surface of the closure seat 73 and the spacer 76.

According to the preferred embodiment of the present invention, as shown in FIGS. 2 to 5, the spacer 76 is integrally extended downwardly from a bottom end of the sealing member 75 to form a U-shaped body.

As shown in FIG. 2, the liquid form medicine 80 is sucked in through the hollow needle 30 to fill between the hollow plunger 70 and the mounting seat 60 inside the barrel 20. When the hollow plunger 70 is pushed down gradually, the medicine 80 is pushed to eject through the hollow needle 30 which is penetrated into a patient's tissue. As shown in FIG. 3, when the plunger 70 is fully pushed down until the spacer 76 is in contact with a top surface 64 of the mounting seat 60, all medicine is ejected and then the needle 30 can be withdrawn from the patient's tissue. At this moment, the pressing wings 743 are inserted into the top end portion 611 of the O-ring passage 61 and in contact with O-ring 50. Moreover, during the sucking operation and the ejecting operation of the syringe 10, the locking latch 821 of the resilient arm 82 is biased against the inner annular wall 201 of the hollow barrel 20 in a slidably movable manner. Therefore, the resilient arm 82 will be slightly pushed inward to the receiving cavity 700 of the hollow plunger 70 to store the resilient force of the resilient arm 82.

After the user completely pulls out the hollow 30 from the patient, the user can immediately apply an additional force to push in the hollow plunger 70 that will deform the spacer 76 and compress the air layer 761, wherein the air inside the air layer 761 may escape through the air apertures 732 into the receiving cavity 700 of the hollow plunger 70. Therefore, the pushing stud 742 can thus be further downwardly pressed against the tip head 31 of the hollow needle 30 to push the tip head 31 and compress the compression spring 40 to store a resilient force, as shown in FIG. 3. At the same time, the pressing wings 743 will also be downwardly pressed against the O-ring 50 rested around the ring groove 32 towards the needle hub 23.

Moreover, as shown in FIG. 4, the engagement of tip head 31 within the O-ring passage 61 is arranged in such a manner that after the O-ring 50 is pushed by the pressing wings 743 to travel through of the O-ring passage. 61, the compression spring 40 can be continuously compressed until its resilient force is increased to a force larger than the predetermined pound of urging force required to break the connecting rib 741. At this movement, the O-ring 50 is pushed out of the O-ring passage 61 so that the engagement of the O-ring 50 between the ring groove 32 of the tip head 31 and the annular wall 612 of the O-ring passage 61 is released. Then, the resilient force stored in the compression spring 40 will upwardly push the tip head 31 of the hollow needle 30 to press against the pusher member 74 until its connecting rib 741 is broken to open the entrance aperture 731, so that the hollow needle 30, the pusher member 74 and the compression spring 40 will all be retracted into the receiving cavity 700 of the hollow plunger 70 automatically.

Furthermore, the additional force for pushing the hollow plunger 70 inward will also slidably drive the resilient arm 82 on the hollow plunger 70 towards the locking stopper 81 on the hollow barrel 20 until the locking latch 821 of the resilient arm 82 received in the locking groove 811, as shown in FIG. 4. At this moment, the resilient arm 82 will be automatically rebounded to its original form that the blocking surface 822 of the resilient arm 82 is biased against the blocking shoulder 812 of the locking stopper 81. Therefore, the hollow plunger 70 is interlocked up with the hollow barrel 20 in a radially movable manner so as to prevent the hollow plunger 70 pulling out of the hollow barrel 20. It is worth to mention that the hollow plunger 70 is pushed at the most inward position of the hollow barrel 20, which cannot be further traveled through the hollow barrel 20 inwardly. In other words, the hollow plunger 70 is locked not only its inward radial movement by the top surface 64 of the mounting seat 60 but also its outward radial movement by the plunger anti-detachment mechanism 80.

In other words, the locking stopper 81 is provided on the annular wall 201 of the hollow barrel 20 at a position that when the hollow plunger 70 is pushed into the hollow barrel 20 for emptying all liquid form medicine therein, the locking latch 821 of the resilient arm 81 is remained in the unlocked position. Until the hollow needle 30 is retracted in the receiving cavity 700 of the hollow plunger 70 by the needle retraction arrangement 1, the locking latch 821 of the resilient arm 82 is blocked by the blocking shoulder 812 of the locking stopper 81, so as to interlock the hollow plunger 70 with the hollow barrel 20.

Moreover, since the hollow plunger 70 is interlocked with the hollow barrel 20 at the inner annular wall 201 thereof, the hollow plunger 70 cannot be unlocked unless the hollow barrel 20 is broken. Therefore, the plunger anti-detachment mechanism 80 can guarantee that the syringe 10 cannot to be re-used once the hollow plunger 70 is locked.

Figure 5:
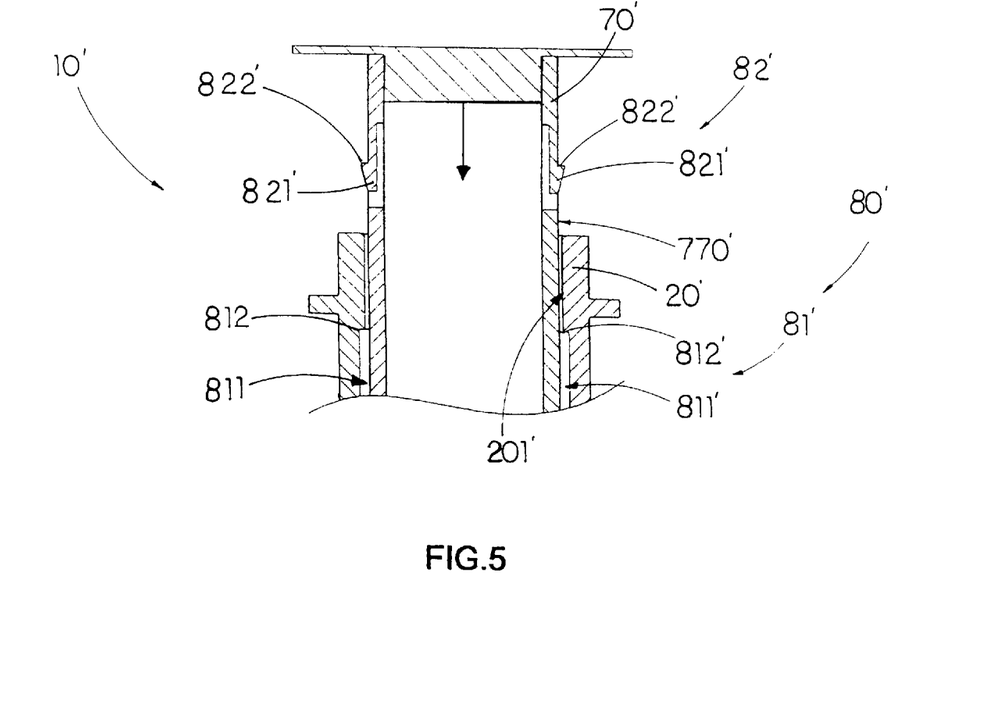
FIG. 5 is a partial sectional view of a syringe in an unlocked position according to a second preferred embodiment of the present invention.

Referring to FIG. 5, a second embodiment of the syringe 10' illustrates an alternative mode of the plunger anti-detachment mechanism 80' of the present invention, wherein the syringe 10' has the same structure of the first embodiment in order to retract the hollow needle 20. The only difference is that the location of the plunger anti-detachment mechanism 80' to interlock the hollow plunger 70 with the hollow barrel 20.

According to the second embodiment, the resilient arm 82' is radially and outwardly extended along the annular wall 770' of the hollow plunger 70' at the outer closed end 71' thereof.

The locking stopper 81' contains a locking groove 811' radially indented on the inner annular wall 201' of the hollow barrel 20' to define the blocking shoulder 812' which is positioned closed to the open end portion 21' of the hollow barrel 20'.

Figure 6:
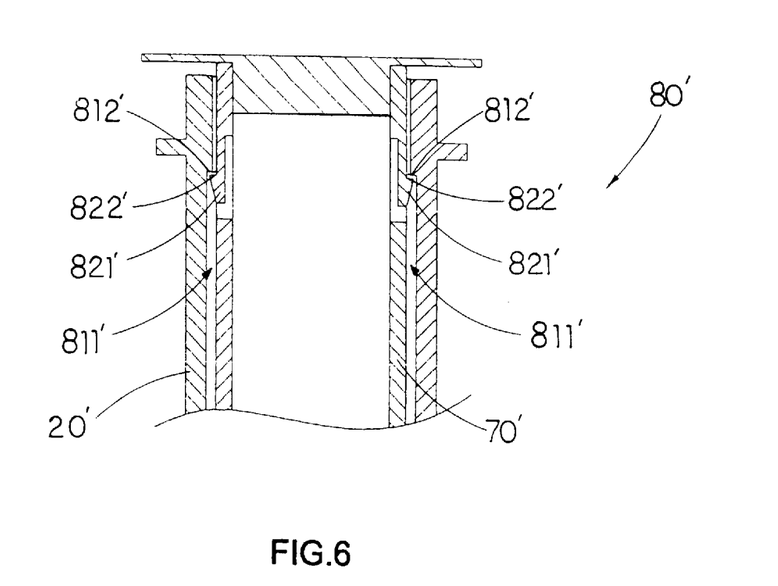
FIG. 6 is a partial sectional view of the syringe in a locked position according to the above second preferred embodiment of the present invention.

Therefore, during the sucking operation of the syringe 10', the resilient arm 82' will be pulled out of the hollow barrel 20' when the hollow plunger 70' is pulled outwardly from the hollow barrel 20'. Furthermore, when all the medicine is ejected the locking latch 821' is still positioned out of the hollow barrel 20'. Therefore, when an additional force is applied to push into the hollow barrel 20' to retract the hollow needle 30', the resilient arm 82' is slidably pushed into the hollow barrel 20 along the annular wall 201 thereof which forces the resilient arm 82' moved into the receiving cavity 700 of the hollow plunger 70'. Then, when the locking latch 821' of the resilient arm 82' is moved inwardly until it reaches the locking groove 811', the blocking surface 822' of the resilient arm 82' will bias against the blocking shoulder 812' of the locking groove 811' to interlock the hollow plunger 70' with the hollow barrel 20', as shown in FIG. 6.

Figure 7:
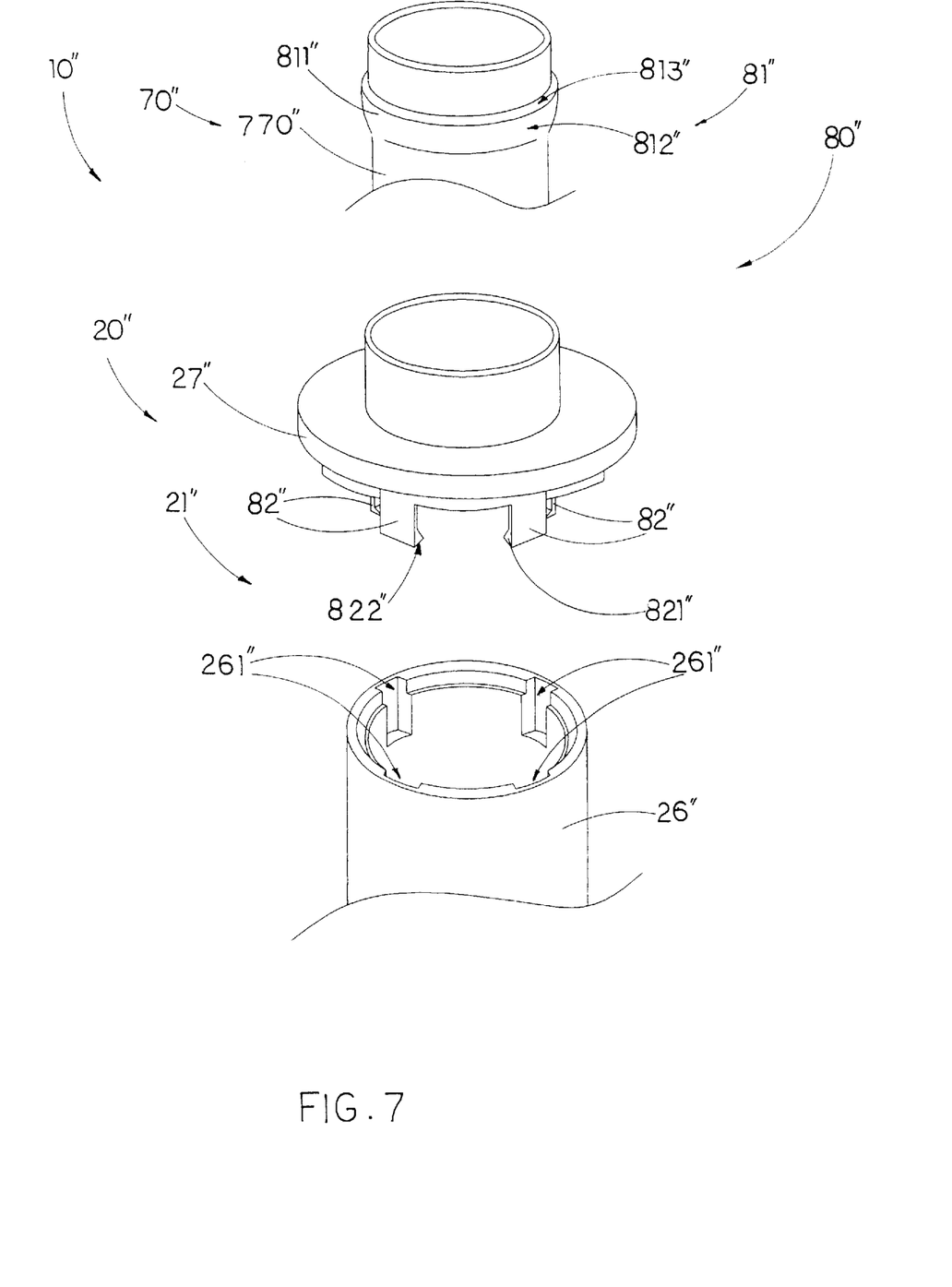
FIG. 7 is a partially exploded perspective view of a syringe according to a third preferred embodiment of the present invention.

As shown in FIG. 7, a third embodiment of the syringe 10" illustrates an alternative mode of the first embodiment of the present invention, wherein the syringe 10" basically has the same structure of the first embodiment to retract the hollow needle 30. The syringe 10" of the third embodiment illustrates that the locking stopper 81" is provided on the outer annular wall 770" of the hollow plunger 70" and the resilient arm 82" is provided on the inner wall 201" of the hollow barrel 20" wherein the locking latch 821" is radially and inwardly extended from the free end of the resilient arm 82".

Figure 8:
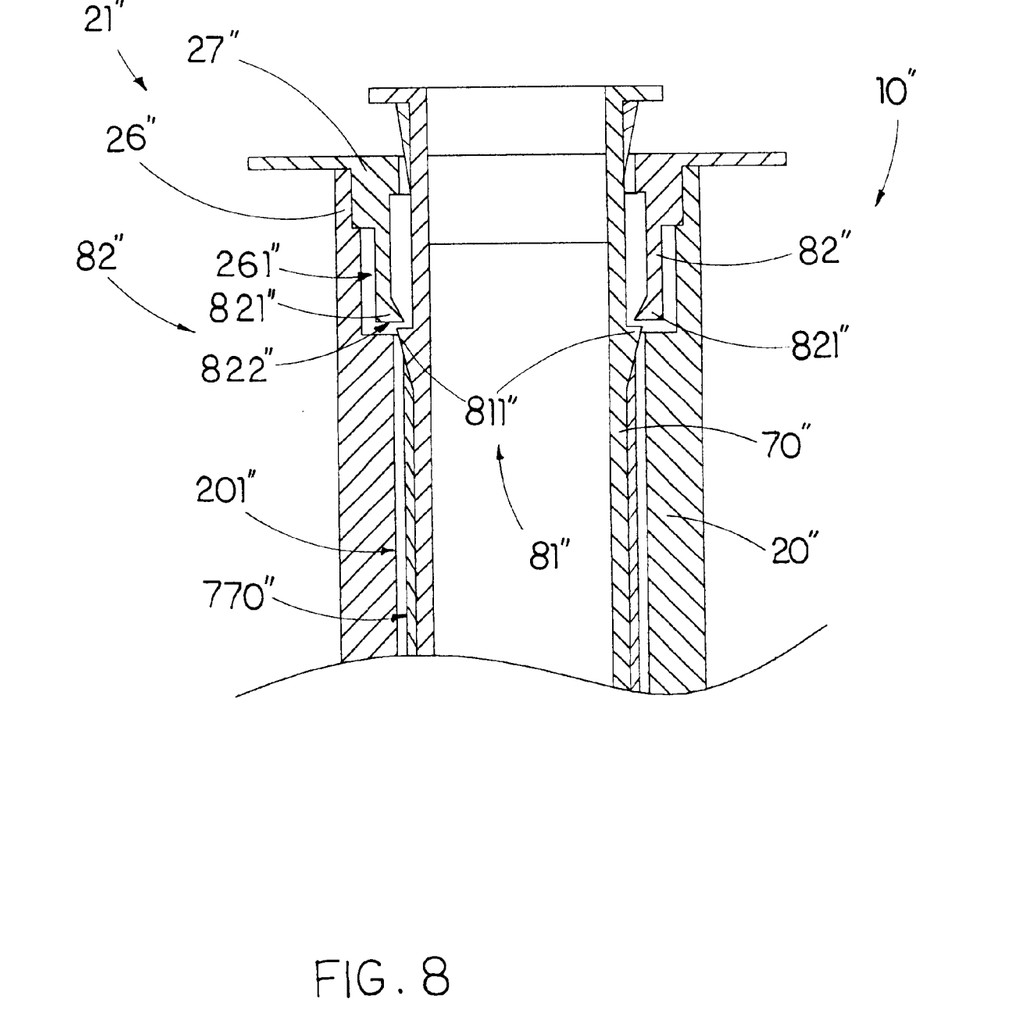
FIG. 8 is a partial sectional view of the syringe according to the above third preferred embodiment of the present invention.

Accordingly, the locking stopper 81" comprises a ring-shaped locking projection 811" radially and inwardly protruded from the outer annular wall 770" of the hollow plunger 70". Preferably, the locking projection 811" having a tapered shaped has a thickness gradually increasing from a top end to a bottom end to define a slanted slider surface 812" and a top locking surface 813" wherein the locking latch 821' of the resilient arm 82' is adapted to glidably pass on the slider surface 812" of the locking projection 811" until the blocking surface 822" of the locking latch 821" biases against the locking surface 813" of the locking projection 811", so as to interlock the hollow plunger 70' with the hollow barrel 20, as shown in FIG. 8.

The hollow barrel 20" according to the third embodiment is constructed to have a tubular barrel body 26" and a ring-shaped handle cap 27" integrally attached to the barrel body 26" in an air tight manner to form the open end portion 21" of the hollow barrel 20" wherein at least a slider groove 261" is radially extended on the inner annular wall 201" of the barrel body 26".

The resilient arm 82" is integrally and downwardly extended from the handle cap 27" and arranged to receive in the slider groove 261" in a radially movable manner when the handle cap 27" is coaxially attached to the barrel body 26" in such a manner that when the locking latch 821" of the resilient arm 82" slidably passes the locking projection 811", the blocking surface 822" of the resilient arm 82" is biased against the locking projection 811" so as to interlock the hollow plunger 70" with the hollow barrel 20" in an axially movable manner.

It is worth to mention that the slider groove 261" has a predetermined size to provide a clearance for the resilient arm 82" radially moving outwardly when the locking latch 821" slides on the outer annular wall 770" of the hollow plunger 70". In other words, the resilient arm 82" is slightly bent outward when the locking latch 8221" slides on the outer annular wall 770" of the hollow plunger 70". After the locking latch 821" passes the locking projection 811", the resilient arm 82" will be automatically rebounded to its original form, so as to interlock the locking latch 821" with the locking stopper 81".

It is obvious that the plunger anti-detachment mechanism of the present invention is capable of incorporating with a conventional syringe without the needle retraction arrangement since the purpose of the plunger anti-detachment mechanism is to interlock the plunger with the hollow barrel so as to prevent the plunger being taken out of the barrel after the syringe is used.

What is claimed is:

1. A syringe, comprising:
    a hollow barrel having an open end portion, a needle mounting portion, and a tubular needle hub extending from said needle mounting portion to provide a needle passageway therethrough;
    a hollow needle having a tissue penetrating end and a tip end thereof affixed with a cylindrical tip head, wherein said tip head of said hollow needle is disposed in said needle mounting portion with said tissue penetrating end penetrating through said needle passageway;
    a mounting seat integrally affixed within said needle mounting portion of said hollow barrel for securely mounting said tip head of said hollow needle in position;
    a hollow plunger adapted to travel through said hollow barrel, said hollow plunger having an outer closed end and an inner end inserted in said hollow barrel through said open end portion of said hollow barrel;
    a needle retraction arrangement received in said hollow barrel for retracting said hollow needle into said hollow plunger; and
    a plunger anti-detachment mechanism, comprising:
        at least a locking stopper radially extended on said hollow barrel; and
        at least a resilient arm, having a locking latch outwardly extended therefrom, radially extended from said hollow plunger wherein said resilient arm is adapted to move from an unlocked position to a locked position, wherein at said unlocked position, said locking latch of said resilient arm is moved away from said locking stopper such that said hollow plunger is capable of freely traveling through said hollow barrel in a coaxially movable manner, and that at said locked position, said hollow needle is retracted in said hollow plunger and said locking latch of said resilient arm is extended to said locking stopper so as to block an axial movement of said hollow plunger with respect to said hollow barrel, so that said hollow plunger is interlocked with said hollow barrel to retain said hollow needle in said hollow plunger.

2. A syringe, as recited in claim 1, wherein said locking stopper is provided at an inner annular wall of said hollow barrel and said resilient arm is provided on an outer annular wall of said hollow plunger in such a manner that said locking latch is adapted to freely slide along said inner annular wall of said hollow barrel in said unlocked position until said locking latch slidably passes said locking stopper.

3. A syringe, as recited in claim 2, wherein said locking stopper contains a locking groove radially indented on said inner annular wall of said hollow barrel and positioned close to said needle mounting portion thereof to define a blocking shoulder to interlock with said hollow plunger, so as to block said axial movement of hollow plunger.

4. A syringe, as recited in claim 3, wherein said resilient arm is integrally extended on said outer annular wall of said hollow plunger and positioned close to said inner end thereof in a radially movable manner wherein a free end of said resilient arm forms said locking latch to interlock with said blocking shoulder of said locking stopper.

5. A syringe, as recited in claim 4, wherein said locking latch having a triangular shape defines a blocking surface thereof in such a manner that when said hollow plunger is pushed down until said locking latch fits in said locking groove, said blocking surface of said resilient arm is biased against said blocking shoulder to interlock said hollow plunger with said hollow barrel.

6. A syringe, as recited in claim 2, wherein said locking stopper contains a locking groove radially indented on said inner annular wall of said hollow barrel and positioned closed to said open end portion thereof to define a blocking shoulder to interlock with said hollow plunger, so as to block said axial movement of hollow plunger.

7. A syringe, as recited in claim 6, wherein said resilient arm is integrally extended on said outer annular wall of said hollow plunger and positioned closed to said outer closed end thereof in a radially movable manner wherein a free end of said resilient arm forms said locking latch to interlock with said blocking shoulder of said locking stopper.

8. A syringe, as recited in claim 7, wherein said locking latch having a triangular shape defines a blocking surface thereof in such a manner that when said hollow plunger is pushed down until said locking latch fits in said locking groove, said blocking surface of said resilient arm is biased against said blocking shoulder to interlock said hollow plunger with said hollow barrel.

9. A syringe, comprising:
 a hollow barrel having an open end portion, a needle mounting portion, and a tubular needle hub extending from said needle mounting portion to provide a needle passageway therethrough;
 a hollow needle having a tissue penetrating end and a tip end thereof affixed with a cylindrical tip head, wherein said tip head of said hollow needle is disposed in said needle mounting portion with said tissue penetrating end penetrating through said needle passageway;
 a mounting seat integrally affixed within said needle mounting portion of said hollow barrel for securely mounting said tip head of said hollow needle in position;
 a hollow plunger adapted to travel through said hollow barrel, said hollow plunger having an outer closed end and an inner end inserted in said hollow barrel through said open end portion of said hollow barrel;
 a needle retraction arrangement received in said hollow barrel for retracting said hollow needle into said hollow plunger; and
 a plunger anti-detachment mechanism, comprising:
  at least a locking stopper radially extended on said hollow plunger; and
  at least a resilient arm, having a locking latch inwardly extended therefrom, radially extended from said hollow barrel wherein said resilient arm is adapted to move from an unlocked position to a locked position, wherein at said unlocked position, said locking latch of said resilient arm is moved away from said locking stopper such that said hollow plunger is capable of freely traveling through said hollow barrel in a coaxially movable manner, and that at said locked position, said hollow needle is retracted in said hollow plunger and said locking latch of said resilient arm is extended to said locking stopper so as to block an axial movement of said hollow plunger with respect to said hollow barrel, so that said hollow plunger is interlocked with said hollow barrel to retain said hollow needle in said hollow plunger.

10. A syringe, as recited in claim 9, wherein said locking stopper is provided at an outer annular wall of said hollow plunger and said resilient arm is provided on an inner annular wall of said hollow barrel in such a manner that said locking latch is adapted to freely slide along said outer annular wall of said hollow barrel in said unlocked position until said locking latch slidably passes said locking stopper.

11. A syringe, as recited in claim 10, wherein said locking stopper comprises a ring-shaped locking projection radially and outwardly protruded from said outer annular wall of said hollow plunger and arranged to interlock with said locking latch of said resilient arm to block said axial movement of said hollow plunger.

12. A syringe, as recited in claim 11, wherein said locking projection having a tapered shape has a thickness gradually increasing from a top end to a bottom end to define a slanted slider surface and a top locking surface, wherein said locking latch of said resilient arm is adapted to slidably pass on said slider surface of said locking projection and to be blocked by said locking surface thereof, so as to interlock said hollow plunger with said hollow barrel.

13. A syringe, as recited in claim 10, wherein said hollow barrel is constructed to have a tubular barrel body and a ring-shaped handle cap integrally attached to said barrel body in an air tight manner to form said open end portion of said hollow barrel, at least a slider groove being radially extended on said inner annular wall of said barrel body, said resilient arm being integrally and downwardly extended from said handle cap in such a manner that when said handle cap is coaxially attached to said barrel body, said resilient arm is received in said slider groove in a radially movable manner.

14. A syringe, as recited in claim 11, wherein said hollow barrel is constructed to have a tubular barrel body and a ring-shaped handle cap integrally attached to said barrel body in an air tight manner to form said open end portion of said hollow barrel, at least a slider groove being radially extended on said inner annular wall of said barrel body, said resilient arm being integrally and downwardly extended from said handle cap in such a manner that when said handle cap is coaxially attached to said barrel body, said resilient arm is received in said slider groove in a radially movable manner.

15. A syringe, as recited in claim 12, wherein said hollow barrel is constructed to have a tubular barrel body and a ring-shaped handle cap integrally attached to said barrel body in an air tight manner to form said open end portion of said hollow barrel, at least a slider groove being radially extended on said inner annular wall of said barrel body, said resilient arm being integrally and downwardly extended from said handle cap in such a manner that when said handle cap is coaxially attached to said barrel body, said resilient arm is received in said slider groove in a radially movable manner.

16. A syringe, as recited in claim 13, wherein said slider groove has a predetermined size to provide a clearance for said resilient arm radially moving outwardly when said locking latch slides on said outer annular wall of said hollow plunger.

17. A syringe, as recited in claim 14, wherein said slider groove has a predetermined size to provide a clearance for said resilient arm radially moving outwardly when said locking latch slides on said outer annular wall of said hollow plunger.

18. A syringe, as recited in claim 15, wherein said slider groove has a predetermined size to provide a clearance for said resilient arm radially moving outwardly when said locking latch slides on said outer annular wall of said hollow plunger.

19. A syringe, as recited in claim 15, wherein said locking latch having a triangular shape defines a blocking surface thereof in such a manner that when said hollow plunger is pushed down until said locking latch passes said locking stopper, said blocking surface of said resilient arm is biased against said blocking stopper to interlock said hollow plunger with said hollow barrel.

20. A syringe, as recited in claim 18, wherein said locking latch having a triangular shape defines a blocking surface thereof in such a manner that when said hollow plunger is pushed down until said locking latch passes said locking stopper, said blocking surface of said resilient arm is biased against said blocking stopper to interlock said hollow plunger with said hollow barrel.

\* \* \* \* \*